United States Patent [19]

Suzuki

[11] Patent Number: 5,744,699
[45] Date of Patent: Apr. 28, 1998

[54] METHOD AND APPARATUS FOR ADSORPTION MEASUREMENT USING TEMPERATURE-COMPENSATED CONSTANT-VOLUME ADSORPTION APPARATUS

[76] Inventor: Isao Suzuki, 3233-9 Tsurutamachi, Utsunomiya-shi, Tochigi-ken, Japan, 320

[21] Appl. No.: 608,532

[22] Filed: Feb. 28, 1996

[30] Foreign Application Priority Data

Mar. 2, 1995 [JP] Japan .................... 7-066713

[51] Int. Cl.[6] .................................. G01N 15/08
[52] U.S. Cl. ............................. 73/38; 73/865.5
[58] Field of Search ..................... 73/38, 865.5

[56] References Cited

U.S. PATENT DOCUMENTS

| | | | |
|---|---|---|---|
| 4,972,730 | 11/1990 | Camp et al. | 73/865.5 |
| 5,074,146 | 12/1991 | Orr et al. | 73/149 |
| 5,133,219 | 7/1992 | Camp | 73/865.5 |

OTHER PUBLICATIONS

Suzuki, "*Temperature–Compensated, Differential Tensimeter For Measuring Gas Adsorption By Low Surface Area Solids*", Rev. Sci. Instrum. 53(7), Jul. 1982, pp. 1061–1066.
Suzuki et al., "*Direct Determination Of Effective Bet–Area Of Xe, Kr, and Ch$_4$*", Journal of Catalysis 155, 163–165 (1995).

Suzuki, "*Measurement of 1 cm$^2$ Surface Areas By Krypton Adsorption Using An Adsorption Apparatus With A Temperature–Compensated, Differential Tensimeter Of Symmetrical Design*", Rev. Sci. Instrum. 66 (10), Oct. 1995, pp. 5070–5074.

*Primary Examiner*—Hezron E. Williams
*Assistant Examiner*—Jay L. Politzer
*Attorney, Agent, or Firm*—Wenderoth, Lind & Ponack

[57] ABSTRACT

A method and an apparatus for adsorption measurement suitable for a small-surface area determination are disclosed. The apparatus includes (a) a temperature-compensated constant-volume adsorption apparatus including: a pair of a reference buret and a sample buret of almost equal shapes and volumes disposed in a lateral symmetry, a pair of a reference adsorption cell and a sample adsorption cell of almost equal shapes and volumes disposed in a lateral symmetry and connected to the reference and sample burets, respectively, the sample cell containing a sample for adsorption measurement, an adsorbate gas supply connected to the reference and sample burets so as to supply an adsorbate gas to the burets, and a pressure gage capable of measuring pressures within the reference and sample burets. The measurement includes the steps of (b) introducing an adsorbate gas into the burets, (c) causing the adsorbate gas in the burets to expand into the respective adsorption cells, and (d) determining an adsorbed amount of the adsorbate gas by the sample cell based on a pressure difference between the burets while compensating for an adsorbed amount by the reference adsorption cell.

9 Claims, 5 Drawing Sheets

METHOD AND APPARATUS FOR ADSORPTION MEASUREMENT USING TEMPERATURE-COMPENSATED CONSTANT-VOLUME ADSORPTION APPARATUS

FIELD OF THE INVENTION AND RELATED ART

The present invention relates to a method and an apparatus for adsorption measurement in a constant volume-system suitable for determining the surface area of a sample having a surface area as small as 3000 cm$^2$ or smaller, particularly 100 cm$^2$ or smaller.

Constant-volume adsorption methods including the BET method, as a representative, have been widely used principally for determining the (specific) surface area of, e.g., a particulate sample. Such surface area determination or measurement is not only important for performance evaluation of a catalyst at the surface thereof, but also effective for evaluating microscopic unevenness or surface roughness (which can be easily evaluated in terms of a roughness factor determined as a ratio of a surface area determined from a gas adsorption amount to a geometrical surface area), and other surface properties of solid materials.

Herein, the constant-volume adsorption measurement method refers to a method wherein an adsorbate gas confined (at a pressure $p_1$) in a vessel (called a buret) having a constant volume ($V_A$) at a temperature T is caused to expand into a vessel (called an adsorption cell and assumed to have a volume $V_B$) containing a sample adsorbent to have a pressure $p_2$, and the material balance before and after the expansion accompanied with adsorption is taken to determine the adsorbed amount of the adsorbate gas. The best known representative thereof is the BET method using the BET equation as an adsorption isotherm. FIG. 1 shows an outline of an apparatus therefor including a buret $V_A$ and an adsorption cell $V_B$ connected with a pipe equipped with a stop cock C, and a pressure gage P for measuring the pressure in the buret $V_A$. The constant-volume adsorption measurement method is the most popular adsorption measurement method because of its wide applicability and high measurement accuracy.

In the constant-volume adsorption measurement, an adsorbed amount A is basically calculated by the following equation:

$$A = (22414/RT)(p_1 V_A - p_2(V_A + V_B)) \quad (1),$$

wherein R is the gas constant, and the term (22414/RT) is a coefficient for converting the adsorbed gas amount into a volume thereof under the standard state (0° C., 1 atm; abbreviated as STP) based on a molar volume of 22414 STPcm$^3$.

From a measured pressure-dependence of adsorbed amount (i.e., an adsorption isotherm), an adsorbed amount for covering the sample surface with a single layer of adsorbed gas molecules (called a monolayer adsorption) is determined. It is known that this relationship can be represented, e.g., by the following BET infinite layer equation in most cases.

$$A = \frac{A_{ML} \cdot C \cdot p_0 \cdot p}{(p_0 - p)[p_0 + p(C - 1)]}, \quad (2)$$

wherein p ($=p_2$) is an adsorption equilibrium pressure, $p_0$ is a saturated vapor pressure of the adsorbate gas at the temperature, and a ratio x ($=p/p_0$) therebetween is called a relative pressure. A is an equilibrium adsorption, $A_{ML}$ is a monolayer adsorption of the adsorbate gas as mentioned above, and C is a BET constant depending on a difference in heat of adsorption between a first adsorbed molecular layer and a second adsorbed molecular layer thereon.

As is described hereinafter, a linear plot based on the above equation for determining a monolayer adsorption is called a BET plot. The BET plot shows a good linearity in the range of relative pressure ($x=p/p_0$) of 0.05–0.35. The thus-determined monolayer adsorption $A_{ML}$ is multiplied by the cross sectional area of the adsorbate gas molecule to obtain a surface area of the sample.

The nitrogen adsorption method as the most standard BET method is an adsorption measurement method using nitrogen as the adsorbate at liquid nitrogen temperature, and $p_0$ is 760 mmHg. Accordingly, in the nitrogen adsorption method, the adsorption measurement is performed up to $p_2 = 250$ mmHg, but a sample showing a small adsorption provides a small relative difference between the first term $p_1 V_A$ and the second term $p_2 (V_A + V_B)$ in Equation (1), so that the adsorption measurement becomes difficult. In a conventional apparatus, $V_A$ and $V_B$ are respectively on the order of 50 cm$^3$, so that the measurement for a sample having a surface of, e.g., 1 m$^2$ requires to obtain 1 as a difference between 130 and 129. That is, a sample showing a small adsorption requires such a severe subtraction.

As the gas pressure is proportional to a temperature, the temperature control of the apparatus determines the accuracy of measuring the mass of an adsorbate gas and therefore the lower limit of measurable surface area. For these reasons, the lower limit of measurable surface area is ca. 1 m$^2$ according to the conventional constant-volume nitrogen adsorption method.

For alleviating the difficulty in temperature control for adsorption measurement for a sample with a small area according to the conventional constant-volume adsorption method, I have already developed a temperature-compensated constant-volume adsorption apparatus, i.e., an adsorption apparatus designed to compensate for an environmental temperature change which impairs the accuracy for measuring the mass of an adsorbate gas (I. Suzuki, Rev. Sci. Instrum. 53, pp. 1061–1066 (July 1982); Catalyst (in Japanese), 29 (6), pp. 426–429 (1982)). FIG. 2 is a conceptual view of the apparatus. Referring to FIG. 2, the apparatus includes a pair of a reference buret (with a volume $V_A$) and a sample buret ($V_A + DV_A$) of almost equal shapes and volumes and a pair of a reference adsorption cell ($V_B$) and a sample adsorption cell ($V_B + DV_B$) also of almost equal shapes and volumes, which pairs are disposed in a lateral symmetry with a differential pressure gage (DP) disposed therebetween. As a result, even if there is some temperature change, the pressure change in one of a pair of buret-adsorption cell combinations is compensated for with that in the other.

In this case, Equation (1) for determining the adsorption amount A described above is transformed into the following Equation (3):

$$A = (22414/RT)[(V_A + DV_A + V_B + DV_B)Dp - ((V_A DV_B - V_B DV_A)/(V_A + V_B))p_1] \quad (3),$$

wherein Dp is a pressure difference of the adsorbate gas between the reference side and the sample side after an adsorbate gas expansion.

If the apparatus is constituted in a nearly ideal lateral symmetry, $DV_A$ is approximately equal to $DV_B$ which is approximately equal to 0, and the second term of Equation (3) becomes negligible, so that Equation (3) is simplified into Equation (3A) below:

$$A = (22414/RT)(V_A + V_B)Dp \quad (3A)$$

Accordingly, the above-mentioned environmental temperature change having impaired the adsorption measurement accuracy is compensated so that a remarkable improvement in adsorption measurement accuracy is expected.

It has been confirmed that the lower limit of measurable surface area according to nitrogen adsorption at liquid nitrogen temperature has been extended down to 0.03 m$^2$ (300 cm$^2$) by using such a temperature-compensated adsorption apparatus. More specifically, in the case of using a conventional BET adsorption method based on Equation (1), a sample having a surface area of 0.03 m$^2$ requires a subtraction of 129.00 from 129.03 to obtain a difference of 0.03, which is a small value obscured by an error of 0.07° C. (=300×(0.03)/129)) in environmental temperature control when the apparatus of FIG. 1 is used.

On the other hand, if an adsorbate gas having a saturated vapor pressure p$_0$ which is smaller than that of nitrogen (N$_2$) is used, the measurement of a smaller surface area becomes possible. For example, in order to obtain a relative pressure of 0.35 necessary for obtaining a monolayer adsorption A$_{ML}$, an adsorption test up to an equilibrium pressure of 250 mmHg is required in the case of using N$_2$ as an adsorbate but an adsorption test up to an equilibrium pressure of 0.6 mmHg is sufficient in the case of using krypton (Kr) as an adsorbate. This is because krypton has a saturated vapor pressure p$_0$ of 1.8 mmHg at liquid nitrogen temperature, thus giving a relative pressure of 0.35 at 0.6 mmHg. As a result, both the first and second terms in Equation (1) become smaller to provide a smaller measurement error.

For example, in order to obtain a surface area of 0.03 m$^2$ by krypton adsorption, 0.03 is obtained as a difference between 0.48 and 0.45 and this results in a remarkably smaller error than in the case of nitrogen adsorption. For this reason, it has been hitherto practiced to perform a surface area measurement by using a noble gas, such as xenon or krypton, having a small vapor pressure as an adsorbate.

Accordingly, also in the temperature-compensated adsorption apparatus, it is expected that the use of an adsorbate gas having a low saturated vapor pressure such as krypton allows a smaller adsorption measurement and thus a smaller surface area measurement. Actually, however, a BET plot of adsorption obtained by using Equation (3) based on an adsorption measurement performed by using Kr as an adsorbate gas in the temperature-compensated adsorption apparatus noticeably deviated from a linear line, thus failing to obtain a monolayer adsorption A$_{ML}$, as will be shown in an experimental example (FIG. 5) described hereinafter.

SUMMARY OF THE INVENTION

In view of the above-mentioned circumstances, a principal object of the present invention is to provide a method and an apparatus allowing an adsorption measurement for a sample having a further smaller surface area by using a temperature-compensated adsorption apparatus as described above.

As a result of my further study for accomplishing the above object, it has been discovered that the above-mentioned non-linearity of BET plot obtained by using the temperature-compensated adsorption apparatus particularly in combination with an adsorbate gas of a low vapor pressure is caused by the fact that the adsorption of an adsorbate gas onto a surface (of e.g., ca. 15 cm$^2$) of the reference adsorption cell is not negligible in case of adsorption measurement for a sample having a small surface area of ca. 10 cm$^2$ or below, while such an adsorption onto the reference cell surface has been almost non-problematic in the case of a surface area measurement by nitrogen adsorption at liquid nitrogen temperature for a sample of 300 cm$^2$ or larger. It has been further found that a correction of the adsorption of an adsorbate gas onto a reference adsorption cell allows a surface area measurement for a sample having a surface area as small as 1 cm$^2$.

More specifically, according to the present invention, there is provided a method for adsorption measurement, comprising:

(a) providing a temperature-compensated constant-volume adsorption apparatus including:

a pair of a reference buret and a sample buret of almost equal shapes and volumes disposed in a lateral symmetry, a pair of a reference adsorption cell and a sample adsorption cell of almost equal shapes and volumes disposed in a lateral symmetry and connected to the reference and sample burets, respectively, the sample cell containing a sample for adsorption measurement, an adsorbate gas supply connected to the reference and sample burets so as to supply an adsorbate gas to the burets, and a pressure gage capable of measuring pressures within the reference and sample burets, (b) introducing an adsorbate gas into the burets, (c) causing the adsorbate gas in the burets to expand into the respective adsorption cells, and (d) determining an adsorbed amount of the adsorbate gas by the sample cell based on a pressure difference between the burets while compensating for an adsorbed amount by the reference adsorption cell.

According to another aspect of the present invention, there is provided an apparatus for adsorption measurement, comprising:

(a) the above-mentioned temperature-compensated adsorption apparatus, and (b) computing means for determining an adsorbed amount of the adsorbate gas by the sample adsorption cell based on a pressure of the adsorbate gas introduced into the burets and a pressure difference between the burets of the adsorbate gas thus-introduced and then expanded into the reference and sample adsorption cells, respectively, while compensating for an amount of the adsorbate gas adsorbed by the reference adsorption cell.

These and other objects, features and advantages of the present invention will become more apparent upon a consideration of the following description of the preferred embodiments of the present invention taken in conjunction with the accompanying drawings.

PREFERRED EMBODIMENTS OF THE INVENTION

Figure 1:
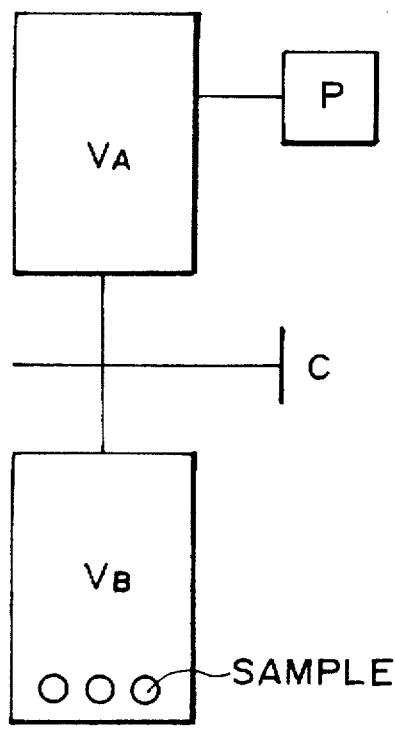
FIG. 1 is a schematic illustration of a conventional constant-volume adsorption apparatus.
Figure 2:
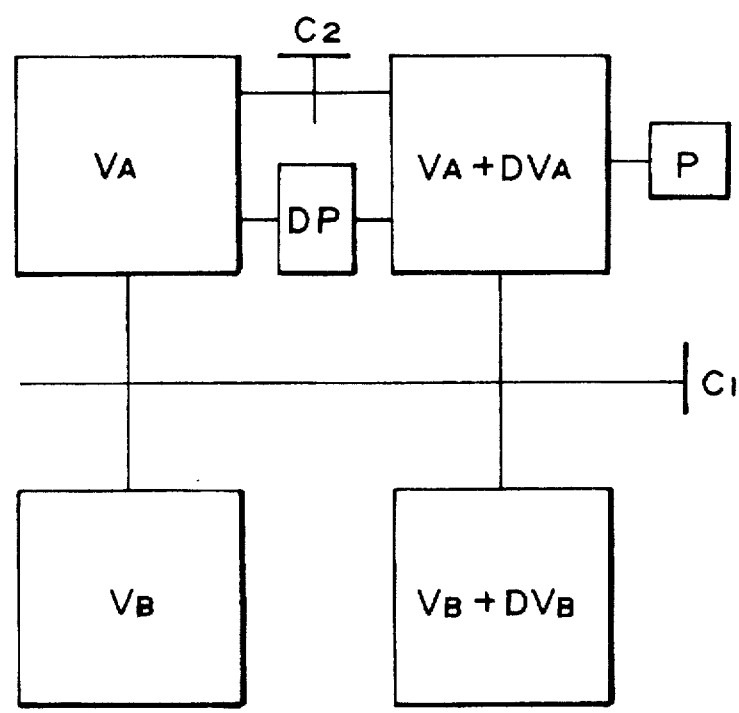
FIG. 2 is a schematic illustration of a temperature-compensated constant-volume adsorption apparatus.
Figure 3:
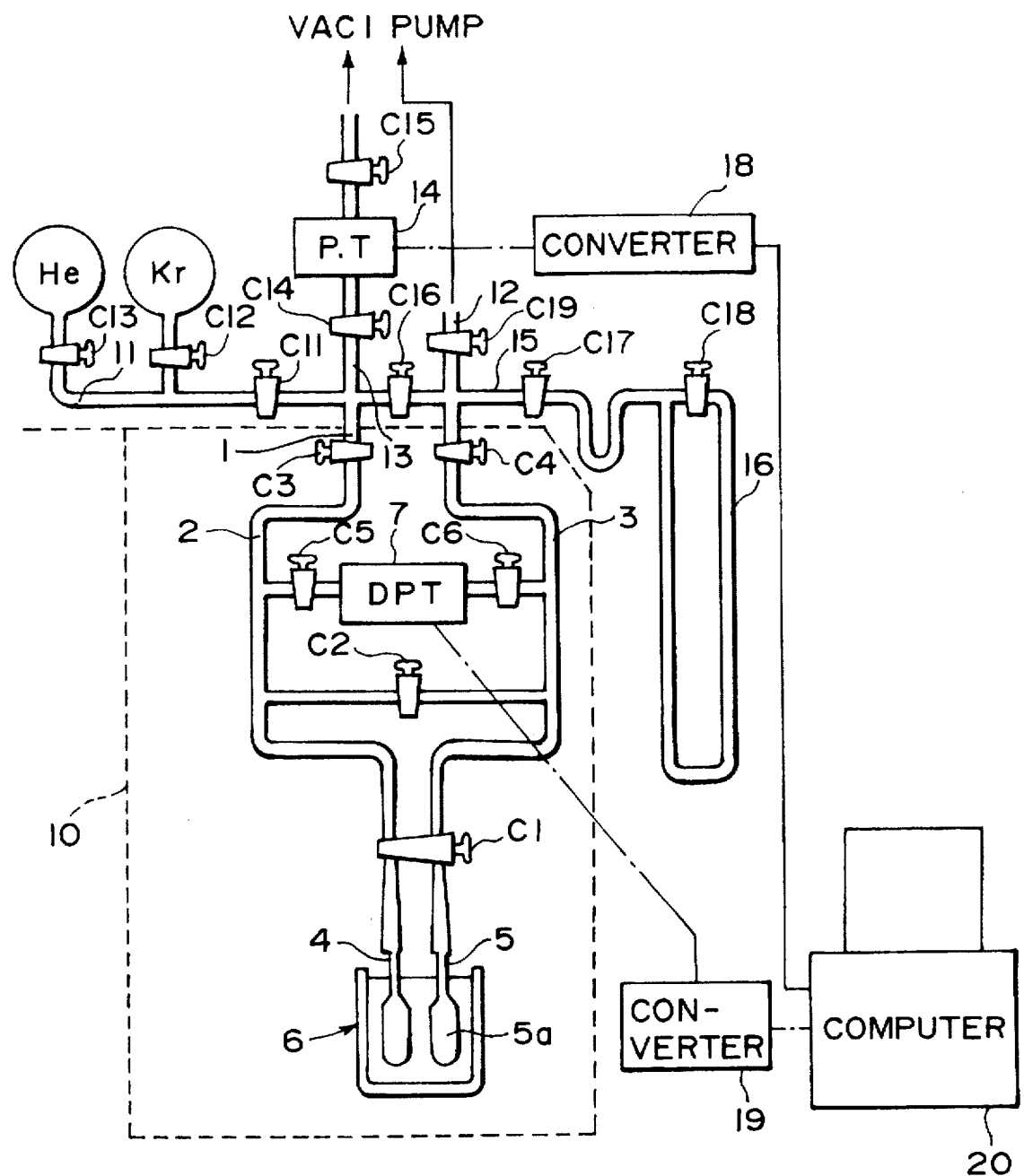
FIG. 3 is a schematic view of an embodiment of the adsorption apparatus according to the invention.

FIG. 3 is schematic view of a preferred embodiment of the apparatus for adsorption measurement according to the present invention including a temperature-compensated adsorption apparatus.

[Apparatus System]

Referring to FIG. 3, a main part 10 of the apparatus includes a PYREX (a borosilicate glass) pipe 1 of 6 mm in inner diameter and stop cocks C1-C6 (and C11-C19 in associated parts), and is connected to a gas supply system via a pipe 11, to a vacuum system VAC1 directly through a pipe 12 equipped with a stop cock C19 and via a low-pressure diaphragm-type pressure gage 14 through a pipe 13 equipped with stop cock C15 and to a high-pressure mercury manometer 16 through a pipe 15 equipped with stop cocks C17 and C18. A portion of the pipe 1 defined by stop cocks C1, C2 and C3 and a diaphragm in a differential pressure gage 7 forms a reference buret 2, and similarly a part of the pipe 1 defined by stop cocks C1, C2 and C4 and the diaphragm in the differential pressure gage 7 forms a sample buret. The reference buret 2 and the sample buret 3 are connected to a reference adsorption cell 4 and a sample adsorption cell 5 containing a sample (adsorbent) 5a, respectively, via a stop cock C1. In a measurement, the adsorption cells 4 and 5 are generally placed within a Dewar vessel 6 filled with liquid nitrogen. In order to improve the temperature-compensation performance, it is preferred to dispose a pair of the burets 2 and 3 and a pair of the adsorption cells 4 and 5 in a lateral symmetry as far as possible and dispose each pair close to each other. The reference buret 2 and the sample buret 3 are communicatably defined from each other by stop cock C2, and a differential pressure gage 7 is disposed between the burets 2 and 3 via stop cocks C5 and C6, respectively.

Outputs of the pressure gage 14 and the differential pressure gage 7 are sent via converters 18 and 19, respectively, for integration and/or A/D conversion to a computer 20 for determining an adsorption (or adsorbed amount) and a surface area as described hereinafter.

Further, it is preferred to cover the burets 2 and 3 and the differential pressure gage 7 with, e.g., aluminum foil, to avoid a temperature change by radiation and minimize the temperature difference between the reference system and the sample system.

[Adsorption Measurement]

In order to perform an adsorption measurement for accurate surface area calculation, it is desired to adopt an accumulative adsorption scheme wherein an adsorption equilibrium pressure is changed after obtaining an adsorbed amount at a certain equilibrium pressure by further introducing an additional amount of the adsorbate gas.

The measurement may perfectly be performed through the following three steps but it will be clarified later that the second step can be omitted.

[1] Measurement of Dead Space Volume (Determination of $V_B$ and $DV_B$ in the Above-Described Equation (3)

(1) The reference adsorption cell 4, reference buret 2, pipe 13 and pressure gage 14 are evacuated to vacuum, and then stop cocks C1, C2, C5, C11 and C16 are closed. An amount of helium is admitted to both the reference buret 2 and the pressure gage 14 to read a pressure $p_1$ thereof by the gage 14. The admitted helium is then caused to expand into the reference adsorption cell 4 by opening cock C1 to read a pressure $p_2$ at that time. Since the adsorption of helium is substantially negligible, the volume $V_B$ of the reference adsorption cell can be evaluated as $V_B=V_0((p_1/p_2)-1)$. wherein $V_0$ is a volume defined by stop cocks C1, C2, C5, C11 and C16 and the diaphragm of the pressure gage 14.

(2) The reference adsorption cell 4, sample adsorption cell 5, reference buret 2 and sample buret 3 are evacuated to vacuum and stop cock C1 is closed. Then, both burets are filled with helium to read a pressure p thereof. Stop cocks C3, C4 and stop cock C2 separating the reference side and the sample side are closed, and then stop cock C1 is opened to allow the helium to expand into the respective adsorption cells 4 and 5, thereby to read a pressure difference (Dp1) between the reference side and the sample side by the differential pressure gage 7. As the reading of the differential pressure gage 7 (Model "P90DL", available from Celesco Sokken K.K.) used in a specific embodiment was affected by an environmental pressure even if a pressure difference between both sides was zero, stop cock C2 was once opened to obtain a pressure difference indication (Dp2, zero point), thereby to obtain a true pressure difference Dp (=Dp1−Dp2) as a subtraction thereof from the previous pressure difference indication (Dp1). As helium is not adsorbed, the material balance of the helium before and after the expansion provides the following Equation (4) with $DV_B$ as an unknown parameter:

$$(V_A+DV_A+V_B+DV_B)(V_A+V_B)Dp=(V_ADV_B-V_BDV_A)p \qquad (4)$$

In case where the absolute value of Dp is large, it is preferred to minimize the absolute value of Dp (and therefore $DV_B$), e.g., by placing clean glass rod pieces at an upper part of the reference adsorption cell or the sample adsorption cell.

[2] Preliminary Adsorption Experiment

Approximate adsorption isotherms $A_R(p)$ and $A_S(p)$ are determined for the reference adsorption cell and the sample adsorption cell, respectively, according to a conventional adsorption method using an adsorbate gas (e.g., Kr) used in a subsequent accurate adsorption experiment. In the case of using the BET infinite adsorption equation (Equation (2) described above), the monolayer adsorption $A_{ML}$ and BET constant C may be determined respectively for the reference system ($A_{MLR}$ and $C_R$) and the sample system ($A_{MLS}$ and $C_S$).

[3] Adsorption Experiment

After evacuating the entire system to vacuum, stop cock C1 is closed and an amount of adsorbate gas (e.g., Kr) is admitted into both burets to read a pressure Pn (1) thereof. Stop cocks C3, C4 and C2 are closed, and then stop cock C1 is opened to allow the adsorbate gas to expand into both adsorption cells. Once a pressure difference is read and then stop cock C2 is opened to read a zero point, which is subtracted from the previous pressure difference reading to provide a true differential pressure $Dp_n$. Then, stop cock C1 is closed. The above operation except for the evacuation to vacuum is repeated to effect an accumulative adsorption operation.

In the course of the accumulative adsorption operation, assuming that the adsorbate gas at a temperature T and a pressure Pn (1) in the burets is allowed to expand into the adsorption cells to obtain a pressure difference $Dp_n$ at an n-th adsorption operation, an adsorbed amount at the n-th adsorption is given by the following equation:

$$A'_n = (22414/RT)[(V_A + DV_A)p_n(1) + (V_B + DV_B)p_{n-1} - (V_A + DV_A + V_B + DV_B)(Pn(2) - Dp_n)], \quad (5)$$

wherein $P_n$ (2) denotes a pressure in the reference adsorption cell after the adsorbate gas expansion and $P_{n-1}$ denotes a pressure of the adsorbate gas remaining in both adsorption cells after the previous (n−1-th) adsorption.

In my previous adsorption determination method before the present invention, the term $p_n$ (2) in the above Equation (5) can be easily calculated because the adsorption onto the reference adsorption cell has been neglected. In the method according to the present invention, however, the adsorption onto the reference adsorption cell is taken into consideration and can be determined from the following equation:

$$(22414/RT)[V_A p_n(1) + V_B p_{n-1} - (V_A + V_B)p_n(2)] = A_R(p_n(2)) - A_R(p_{n-1}) \quad (6),$$

wherein $A_R$ ($p_n$(2)) denotes an isothermally adsorbed amount of the adsorbate gas onto the reference adsorption cell and can be determined based on the BET infinite layer equation (Equation (2) described above) in the case of Kr adsorption.

More specifically, $A_{MLR}$ and $C_R$ are determined in [2] above, and all the terms accompanied with a suffix n−1 are zero at the first adsorption (n=1). Further, in the first adsorption, $p_1$(1) is directly measured and is substituted in the left side of Equation (6) to obtain an equation having an unknown value $p_1$(2), which may be determined by the Newton method. Further, $p_1$ (i.e., the pressure of the adsorbate gas remaining in the adsorption cells after the first adsorption) is determined according to a method described hereinafter, so that an equation having an unknown value $p_2$(2) is obtained and $p_2$(2) may be similarly determined by the Newton method. Accordingly, values $p_3$(2), $p_4$(2), . . . , i.e., $p_n$(2) in general, can be determined sequentially.

Incidentally, at the time of the zero point measurement by opening stop cock C2, the pressure in the reference adsorption cell and the pressure in the sample adsorption cell are equalized. That is, the pressure in the reference adsorption cell is increased from $p_R$ (=$p_n$(2)) by $Dp_R$ to $p_n$, and the pressure in the sample adsorption cell is increased from $p_S$ (=$p_n$(2)−$Dp_n$) by $Dp_S$ to $p_n$. At that time, extra adsorptions occur additionally in the reference adsorption cell and the sample adsorption cell, and the material balance including such extra adsorptions, denoted by $DA_R$ and $DA_S$, may be given by the following equations (7) and (8):

$$(22414/RT)[(V_A + DV_A + V_B + DV_B)p_S + (V_A + V_B)p_R] = (22414/RT)[2V_A + 2V_B + DV_A + DV_B)p_n] + DA_R + DA_S \quad (7)$$

$$p_S + Dp_S = p_R + Dp_R = p_n \quad (8)$$

These correction terms for adsorbed amounts are substantially negligible in adsorption experiments at high pressures but become relatively large in low-pressure experiments.

The extra adsorptions $DA_R$ and $DA_S$ may be given by the following equations based on the adsorption isotherms on the reference side and the sample side, respectively:

$$DA_R = A_R(p_R + Dp_R) - A_R(p_R) \quad (9)$$

$$DA_S = A_S(p_S + Dp_S) - A_S(p_S) \quad (10).$$

If $p_n$(2) is determined according to the above-mentioned method, $P_R$ and $P_S$ for the n-th adsorption operation can be determined. As a result, the above Equations (7) and (8) are reduced to simultaneous equations including unknown parameters $Dp_S$ and $Dp_R$ for an n-th adsorption operation, which can be easily solved by the Newton-Raphson method to determine $Dp_S$ and $Dp_R$. From the determined $Dp_S$ and $Dp_R$, the values of $p_n$, $DA_R$ and $DA_S$ can be determined by Equations (8), (9) and (10).

An accumulated adsorption $A_n$ is given as the sum of an adsorption $\Sigma A'_n$ and an extra adsorption $\Sigma DA_S$ as shown in the following equation:

$$A_n = \Sigma(A'_n + DA_S) \quad (11).$$

The equilibrium pressure at that time is $p_n$.

The above-mentioned computing process may be inclusively summarized as a process of determining $p_n$(2) (and therefore $A'_n$), $DA_R$ and $DA_S$ based on measured values $p_n$(1) and $Dp_n$ supplied to a computer 20 (a personal computer "PC9801DA" available from NEC K.K., in a specific embodiment) by using Equations (2) and (5)−(10) and, based on the determined values, determining $p_n$ and also an accumulated adsorption $A_n$ according to Equation (11).

[Monolayer Adsorption and Surface Area Determination]

Figure 4:
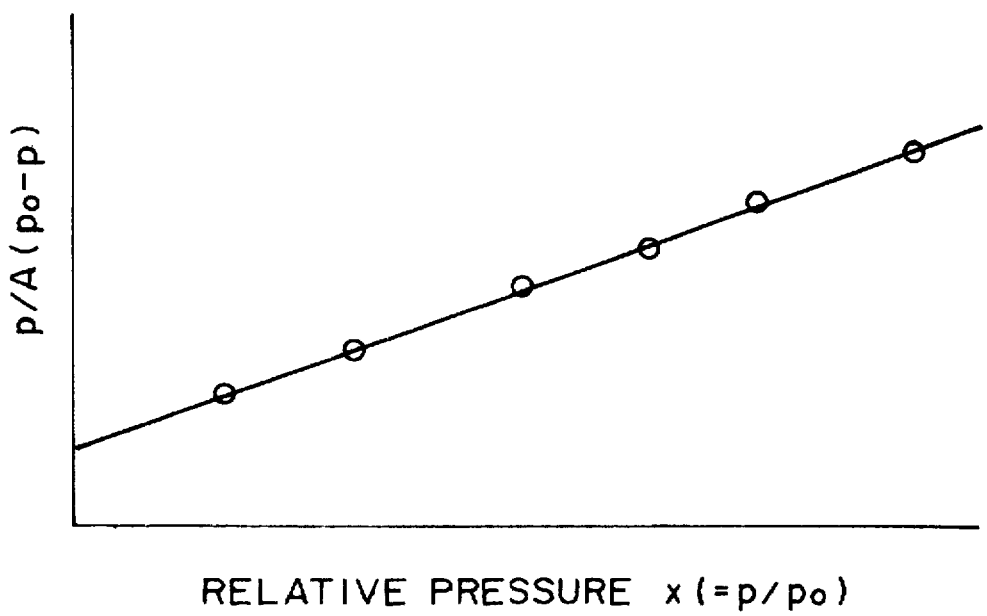
FIG. 4 is a graph showing a BET plot for krypton adsorption onto an empty sample adsorption cell in case of monolayer adsorption onto a reference adsorption cell $A_{MLR}=2.5\times10^{-4}$ STPcm$^3$.
Figure 6:
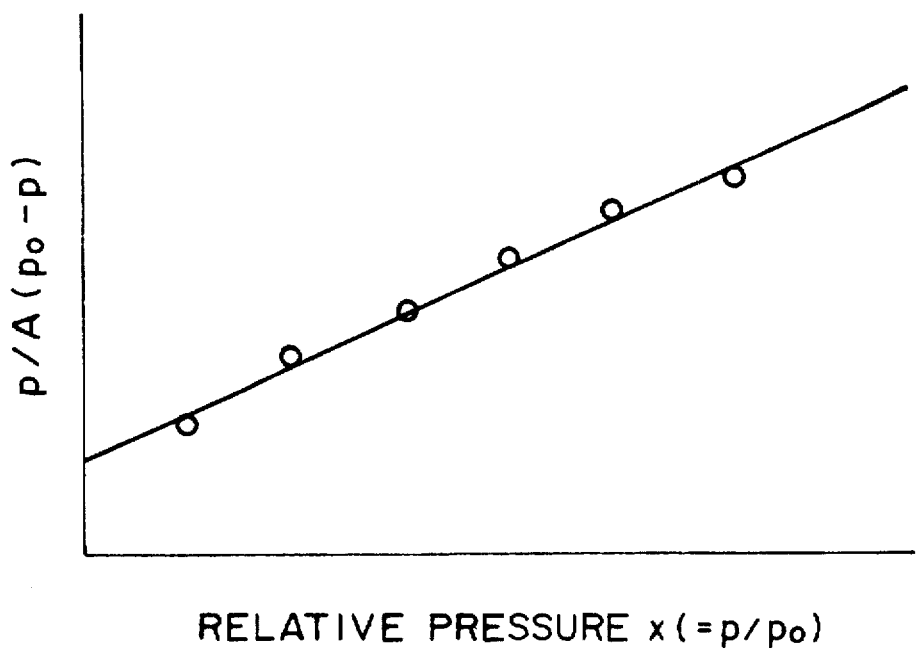
FIG. 6 is a graph showing a BET plot for krypton adsorption onto a sample adsorption cell containing 50 steel balls in case of $A_{MLR}=2.5\times10^{-4}$ STPcm$^3$.

If the accumulated adsorptions A (=$A_n$) are determined at various relative pressures x (=$p_n/p_0$), the values x/A(1−x)= p/A($p_0$−p), for example, are plotted at the respective relative pressures (to provide a BET plot as shown in FIG. 4, FIG. 6, etc., obtained in Examples appearing hereinafter) based on the following formula (12) derived from the above Equation (2) (BET infinite layer formula):

$$x/A(1-x) = 1/(A_{ML}C) + x \cdot (C-1)/(A_{ML}C) \quad (12),$$

thereby to obtain an intercept $1/A_{ML} \cdot C$ and a slope $(C-1)/A_{ML} \cdot C$, from which a monolayer adsorption (in the unit of $STPcm^3$) and a BET constant C are determined.

From the monolayer adsorption $A_{ML}$ thus obtained, a surface area S of the sample is calculated by the following equation:

$$S = a \times 10^{-16} \times (A_{ML}/22414) \times 6.02 \times 10^{23} \quad (13),$$

wherein a denotes a cross-sectional area of one adsorbate gas molecule and may be regarded as 23 ($A^2$) in the case of Kr.

[Example of Adsorption Measurement]

In a specific example, krypton (Kr, having a saturated vapor pressure at liquid nitrogen temperature of $p_0$=1.8 mmHg) was successively adsorbed onto 1 mm-dia. steel balls 5a for ball bearing by using an apparatus shown in FIG. 3, whereby it was confirmed possible to measure a surface area of ca. 1 cm².

The BET infinite layer equation (Equation (2)) was adopted as adsorption isotherms for both the reference adsorption cell and the sample adsorption cell. More specifically, $A_R$ and $A_S$ in Equations (6), (9) and (10) were determined by the BET linear equation (Equation (12)) by using monolayer adsorptions $A_{MLR}$ and $A_{MLS}$ and BET constants $C_R$ and $C_S$ obtained through preliminary experiments as described above. Conventional adsorption tests performed in advance for an empty reference adsorption cell and an empty sample cell showed monolayer adsorptions $A_{MLR}$ and $A_{MLS}$ of both $2.50 \times 10^{-4}$ STPcm³ and BET constants $C_R$ and $C_S$ of both 12. By using these values, krypton adsorption onto the empty sample adsorption cell was performed at liquid nitrogen temperature to provide a BET plot shown in FIG. 4. From the intercept and slope of the BET plot, the krypton monolayer adsorption $A_{ML}$ onto the empty sample adsorption cell was calculated at $2.54 \times 10^{-4}$ STPcm³.

Figure 5:
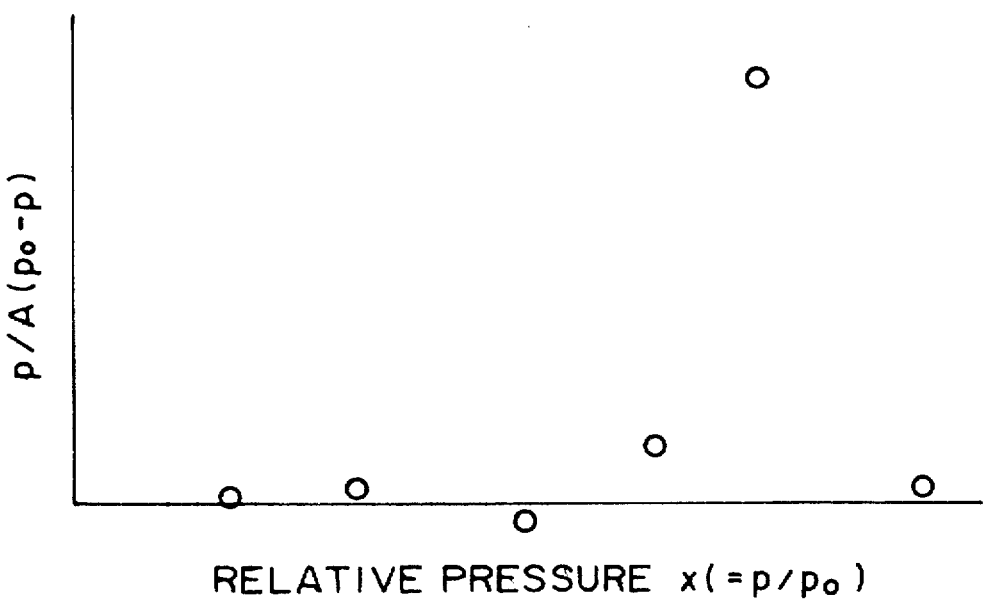
FIG. 5 is a graph showing a BET plot for krypton adsorption onto an empty sample adsorption cell with assumption of monolayer adsorption onto a reference adsorption cell $A_{MLR}=0$.

In this instance, if the krypton adsorption onto the reference adsorption cell is not taken into consideration (i.e., if the calculation is performed on the assumption of $A_{MLR}=0$), the resultant BET plot was remarkably deviated from linearity (FIG. 5), the calculation of the monolayer adsorption was practically impossible. A BET plot for adsorption of xenon having a further lower saturated vapor pressure would presumably provide a further noticeable deviation from linearity.

Further, krypton adsorption onto a sample adsorption cell containing 50 steel balls was performed, and the resultant BET plot is shown in FIG. 6. From the intercept and slope in FIG. 6, the krypton monolayer adsorption $A_{ML}$ onto the sample adsorption cell containing 50 steel balls could be determined.

Figure 7:
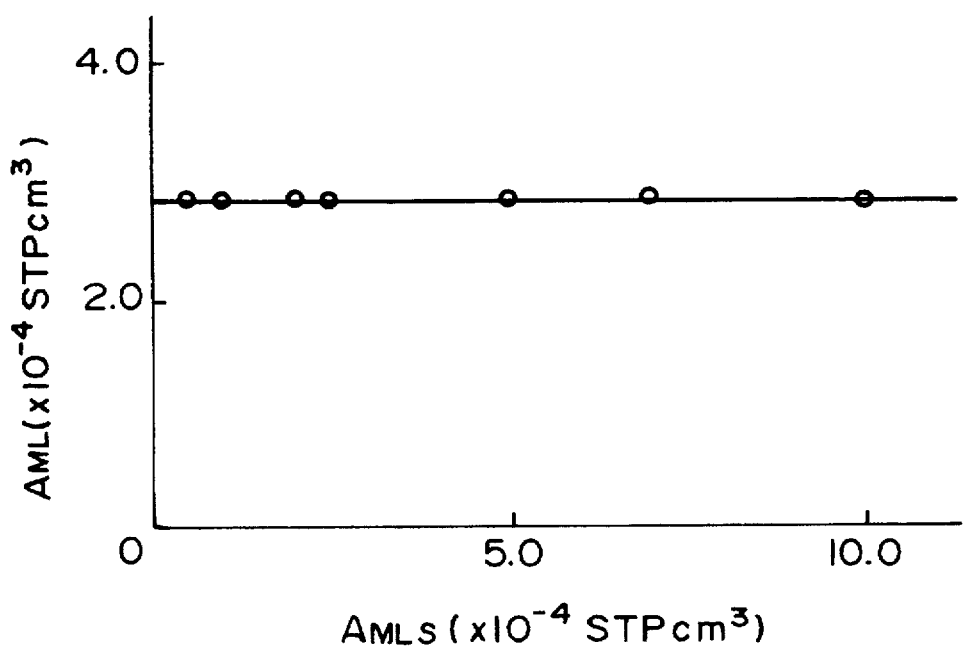
FIG. 7 is a graph showing a relationship between krypton monolayer adsorption $A_{ML}$ onto a sample adsorption cell containing 50 steel balls and $A_{MLS}$ used.

In the above determination of the monolayer adsorption $A_{ML}$ onto the sample adsorption cell, $A_R(p)$ and $A_S(p)$ obtained through preliminary experiments were used. Actually, however, the calculated value of $A_{ML}$ did not substantially vary even if the value of $A_S(p)$, i.e., $A_{MLS}$, was tentatively varied for the calculation (FIG. 7). Thus, it is understood that an approximate value of $A_{MLS}$ is sufficient.

Figure 8:
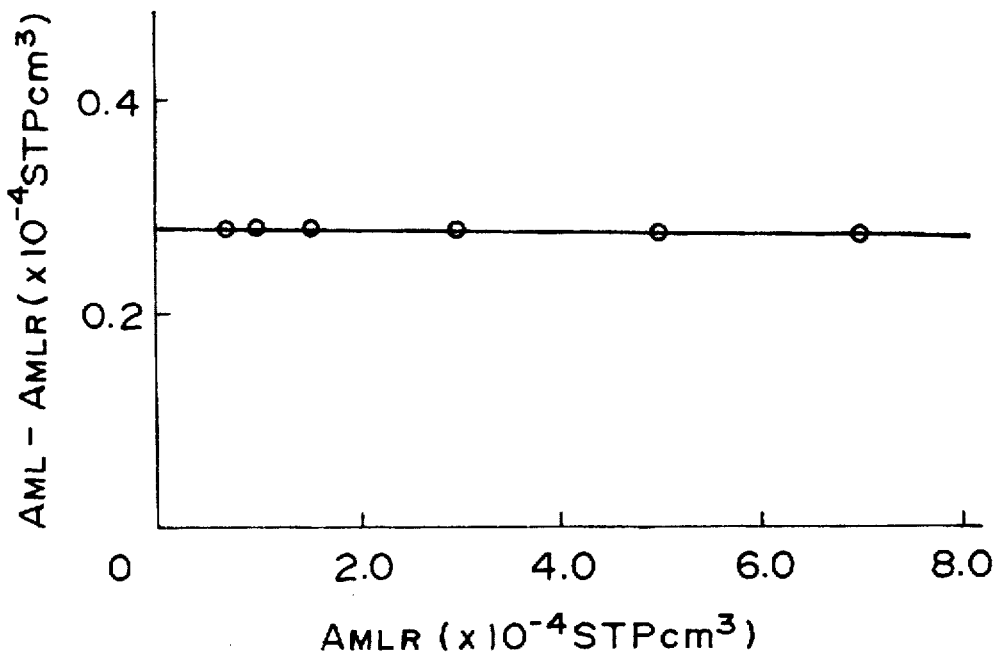
FIG. 8 is a graph showing a relationship between ($A_{ML}-A_{MLR}$) for a sample adsorption cell containing 50 steel balls and $A_{MLR}$ used.

Further, the calculation result of $A_{ML}-A_{MLR}$ did not substantially depend on the values of $A_{MLR}$ used for the calculation (FIG. 8). However, the use of too small $A_{MLR}$ value results in a poor linearity of BET plot as described above, thus failing to allow a reliable determination of $A_{ML}$. The term $A_{ML}-A_{MLR}$ means to determine an adsorbed amount onto a sample adsorption cell with reference to an adsorbed amount onto a reference adsorption cell. An adsorbed amount onto a sample is calculated as a difference between an adsorbed amount onto a sample adsorption cell containing the sample and an adsorbed amount onto the empty sample adsorption cell, which are both determined with reference to $A_{MLR}$ (which can be determined by a preliminary experiment but does not substantially affect the calculated value of the adsorbed amount onto a sample even if an approximate value is used therefor).

Figure 9:
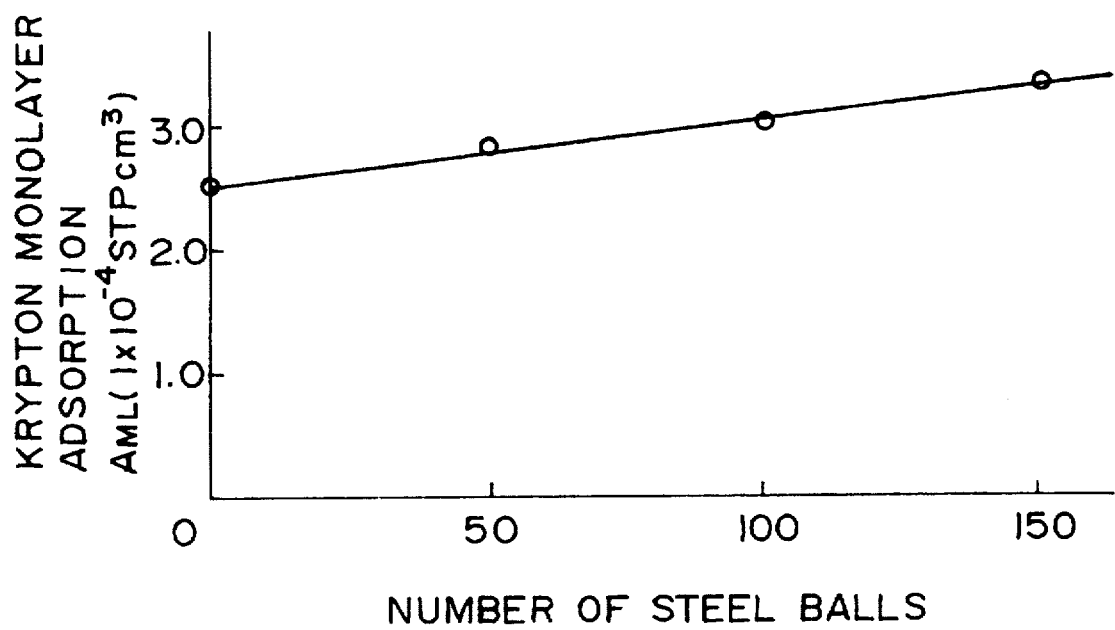
FIG. 9 is a graph showing a relationship between krypton monolayer adsorption $A_{ML}$ onto a sample adsorption cell containing steel balls and the number of steel balls.

FIG. 9 shows a relationship between krypton monolayer adsorptions $A_{ML}$ onto identical sample adsorption cells containing 50, 100 and 150 steel balls, respectively, of 1 mm in diameter and the numbers of the steel balls. The intercept corresponds to a monolayer adsorption onto the empty sample adsorption cell and the slope corresponds to a monolayer adsorption per steel ball. The slope agreed with a value obtained from krypton adsorption onto 10000 identical steel balls by using a conventional adsorption apparatus. In other words, the krypton monolayer adsorptions onto 50, 100 and 150 steel balls agreed with calculated values based on the krypton adsorption onto 10000 steel balls. More specifically, the monolayer adsorption $(A_{ML}-A_{MLR})$ onto 50 steel balls was determined at 0.27 STPcm³, from which the surface area was calculated at 1.7 cm² according to Equation (13). This substantially agreed with a geometrically calculated surface area of the steel balls (1.57 cm²) and clearly shows that the method of the present invention allows a measurement of a surface area on the order of 1 cm².

[Modifications]

In the above, the method and apparatus for adsorption measurement using a temperature-compensated adsorption apparatus and suitable to be applied to a small surface area sample according to the present invention have been described based on a preferred embodiment thereof with reference to FIG. 3 and subsequent figures. It is however believed readily understandable that the above-described embodiment can be modified in various manners within the scope of the present invention. Particularly, the above-mentioned calculation or determination process described based on Equation (5) and subsequent equations allows a strict calculation for ensuring a theoretical accuracy but can be simplified in various manners within an extent of practical measurement accuracy if apparatus characteristics of the temperature-compensated adsorption apparatus are taken into consideration. The following are some examples of such modifications.

(1) The above-described embodiment is applicable not only to surface area measurement but also to a variety of adsorption measurement by using different adsorption isotherms or $A_R$ ($p_R$) and $A_S$ ($p_S$) for the reference adsorption cell and the sample adsorption cell. Particularly, the present invention is expected to be effectively applicable to a water vapor adsorption measurement wherein a large amount of adsorption occurs even onto a reference adsorption cell.

(2) The adsorption temperature is not limited to the liquid nitrogen temperature.

(3) The entire apparatus can of course be made of a metal, such as stainless steel, instead of glass.

(4) A combination of the diaphragm-type pressure gage 14 and the differential pressure gage 7 has been used as a pressure gage used in the above embodiment, but the types of these pressure gages are arbitrary. The mercury manometer 16 can be replaced by a diaphragm-type one allowing the measurement of a pressure up to atmospheric pressure. It is also possible to dispose separate pressure gages for the reference system and the sample system, respectively. By using such separate pressure gages, the preliminary operation for obtaining adsorption isotherms for the reference adsorption cell and the sample adsorption cell ([2] Preliminary adsorption experiment described above) can be replaced with measurement of the pressures of adsorbate gas before and after expansion for the reference system and the sample system, respectively, during the actual adsorption measurement to simultaneously obtain isotherms $A_R(p)$ and $A_S(p)$.

(5) By using a differential pressure gage 7 requiring no zero point correction, the operation of opening stop cock C2 after the adsorption operation for correcting the zero point of the differential pressure gage 7 can be omitted, and correspondingly the calculation based on Equations (7)–(10) becomes unnecessary ($DA_R$ is approximately equal to $DA_S$, which is approximately equal to 0).

(6) As shown in FIGS. 7 and 8, the calculated values of $A_{ML}$ did not essentially depend on $A_R(p)$ and $A_S(p)$, i.e., $A_{MLR}$ and $A_{MLS}$. Accordingly, the experimental operation for determining these parameters (i.e., the above-mentioned [2] Preliminary adsorption experiment) can be omitted and the calculation can be simplified without causing a substantial lowering in measurement accuracy by using an appropriate value of $A_{MLR}$ determined at ca. 1.5 times the geometrical surface area of the reference system and an appropriate value of $C_R$ assumed, e.g., at ca. 10. Further, $A_{MLS}$ and $C_S$ can be assumed at approximate values or can be determined through iterative calculations. In an adsorption measurement using an adsorbate gas having a higher vapor pressure than krypton, the values of $DA_R$ and $DA_S$ are at most ca. 0.1% of $A'_n$ and can be ignored (i.e., the calculation based on Equations (7)–(10) can be omitted). However, these terms may not be negligible in case of xenon.

(7) In order to accurately measure a small pressure difference, the values measured by the differential pressure gage may preferably be integrated by the converter 19 to obtain an average value thereof, but such integration or conversion can be performed as an internal processing in the computer 20 or can be omitted depending on a required level of measurement accuracy.

(8) In the above-mentioned experimental example, the manipulation of the stop cocks was performed manually but an automatic manipulation is of course possible. It is also possible to automatically minimize the absolute values of Dp and/or $DV_B$, i.e., by disposing movable bellows at an upper part of the adsorption cell(s). The measured pressures were inputted through the A/D converter 18 but can be inputted manually to the computer 20.

(9) For measuring a surface area of 10 cm² or less, the adsorbate gas may preferably be Kr ($p_0$=1.8 mmHg) or Xe ($p_0$=0.001 mmHg) at liquid nitrogen temperature, or Xe ($p_0$=0.05 mmHg) at liquid oxygen temperature. For measuring 10–1000 cm², it is preferred to use the above-mentioned adsorbates, or $CH_4$ ($p_0$=10 mmHg) at liquid nitrogen temperature or $CH_4$ ($p_0$=80 mmHg) at liquid oxygen temperature. For measuring a surface area of 1000 cm² or larger, in addition to the above adsorbates, it is possible to use $N_2$ ($p_0$=760 mmHg) or Ar ($p_0$=200 mmHg) at liquid nitrogen temperature, $CO_2$ ($p_0$=760 mmHg) at dry ice temperature, or n—$C_4H_{10}$ ($p_0$=760 mmHg) at freezing point. The above are mere examples, and any adsorbate gas showing a vapor pressure of preferably at most 760 mmHg may be used at an appropriate adsorption temperature while relying on the measurement accuracy-improving effect according to the present invention.

(10) In the above embodiment, the Newton method has been used in order to solve Equations (5), (6), (7) and (8), but it is of course possible to use another numerical calculation method, preferably applicable to a personal computer.

(11) It is also possible to correct the dead space volume and adsorbed amount in the adsorption cells based on consideration of the thermal transpiration effect in case of an adsorption measurement at a low-pressure region of $10^{-1}$ mmHg or below (as reported in Isao Suzuki, et al., J. Catal., 155, pp. 163–165 (1995)).

As described above, according to the method and apparatus for adsorption measurement of the present invention using a temperature-compensated adsorption apparatus, it becomes possible to accurately measure a surface area of a sample having a surface area as small as 10 cm² or below, particularly by using an adsorbate gas having a substantially lower saturated vapor pressure than nitrogen. It has also become possible to allow an accurate evaluation of the surface states of such a sample.

What is claimed is:

1. A method for adsorption measurement, comprising:
   (a) providing a temperature-compensated constant-volume adsorption apparatus including:
      a pair of a reference buret and a sample buret of almost equal shapes and volumes disposed in a lateral symmetry,
      a pair of a reference adsorption cell and a sample adsorption cell of almost equal shapes and volumes disposed in a lateral symmetry and connected to the reference and sample burets, respectively, the sample cell containing a sample for adsorption measurement,
      an adsorbate gas supply connected to the reference and sample burets so as to supply an adsorbate gas to the burets, and
      a pressure gage capable of measuring pressures within the reference and sample burets,
   (b) introducing an adsorbate gas into the burets,
   (c) causing the adsorbate gas in the burets to expand into the respective adsorption cells, and
   (d) determining an adsorbed amount of the adsorbate gas by the sample cell based on a pressure difference between the burets while compensating for an adsorbed amount by the reference adsorption cell, wherein the adsorbed amount of the adsorbate gas by the reference adsorption cell is determined according to the following equation (6):

$$(22414/RT)[V_A P_n(1)+V_B P_{n-1}-(V_A+V_B)P_n(2)]=A_R(P_n(2))-A_R(P_{n-1})\ (6),$$

wherein symbols signify the following:
R: gas constant, T: temperature,
$V_A$: volume of the reference buret,
$V_B$: volume of the reference adsorption cell,
$P_n(1)$: pressure in the burets after introducing the adsorbate gas into the burets prior to an n-th adsorption,
$P_{n-1}$: pressure in the adsorption cells after a previous (n−1)-th adsorption,
$P_n(2)$: pressure in the reference adsorption cell after the n-th adsorption,
$A_R(P_n(2))$: an isothermally adsorbed amount of the adsorbate gas onto the reference adsorption cell after the n-th adsorption,
n: an integer,
provided that $P_{n-1}$ and $A_R(P_{n-1})$ are 0 for n=1.

2. An apparatus for adsorption measurement, comprising:
   (a) a temperature-compensated constant-volume adsorption apparatus including:
      a pair of a reference buret and a sample buret of almost equal shapes and volumes disposed in a lateral symmetry,
      a pair of a reference adsorption cell and a sample adsorption cell of almost equal shapes and volumes disposed in a lateral symmetry and connected to the reference and sample burets, respectively,
      an adsorbate gas supply apparatus connected to the reference and sample burets so as to supply an adsorbate gas to the burets, and a pressure gage capable of measuring pressures within the reference and sample burets, and (b) computing means for determining an adsorbed amount of the adsorbate gas by the sample adsorption cell based on a pressure of the adsorbate gas introduced into the burets and a pressure difference between the burets of the adsorbate gas thus-introduced and then expanded into the reference and sample adsorption cells, respectively, while compensating for an amount of the adsorbate gas adsorbed by the reference adsorption cell, wherein the adsorbed amount of the adsorbate gas by the reference adsorption cell is determined according to the following equation (6):

$$(22414/RT)[V_A P_n(1)+V_B P_{n-1}-(V_A+V_B)P_n(2)]=A_R(P_n(2))-A_R(P_{n-1}) \quad (6),$$

wherein symbols signify the following:
R: gas constant, T: temperature,
$V_A$: volume of the reference buret,
$V_B$: volume of the reference adsorption cell,
$P_n(1)$: pressure in the burets after introducing the adsorbate gas into the burets prior to an n-th adsorption,
$P_{n-1}$: pressure in the adsorption cells after a previous (n−1)-th adsorption,
$P_n(2)$: pressure in the reference adsorption cell after the n-th adsorption,
$A_R(P_n(2))$: an isothermally adsorbed amount of the adsorbate gas onto the reference adsorption cell after the n-th adsorption, n: an integer,
provided that $P_{n-1}$ and $A_R(P_{n-1})$ are 0 for n=1.

3. A method according to claim 1, wherein the adsorbate gas is a gas having a lower saturated vapor pressure than nitrogen at liquid nitrogen temperature.

4. A method according to claim 1, wherein the steps (b) to (d) are repeated for accumulative adsorption.

5. A method according to claim 1, wherein the determination in step (d) includes computerized numerical calculation.

6. A method according to claim 1, wherein the determination in step (d) includes calculation based on the Newton-Raphson method.

7. A method according to claim 1, wherein the determination in step (d) is performed based on the BET infinite layer equation as an adsorption isotherm for the reference adsorption cell and for the sample adsorption cell.

8. An apparatus according to claim 2, wherein said adsorbate gas has a saturated pressure which is lower than that of $N_2$ (760 mmHg) at liquid nitrogen temperature.

9. An apparatus according to claim 2, wherein said pressure gage capable of measuring pressures within the reference and sample burets comprises a pressure gage for measuring a pressure within the reference buret and a differential pressure gage connected between the reference and sample burets.

* * * * *